United States Patent
Kirwan, Jr. et al.

(10) Patent No.: US 9,662,164 B1
(45) Date of Patent: May 30, 2017

(54) ELECTROSURGICAL CABLE CONNECTOR FOR MULTIPLE FORCEPS CONNECTIONS

(71) Applicant: Kirwan Surgicial Products LLC, Marshfield, MA (US)

(72) Inventors: Lawrence T. Kirwan, Jr., Kingston, MA (US); Robert T. Boyd, Kingston, MA (US)

(73) Assignee: Kirwan Surgical Products LLC, Marshfield, MA (US)

( * ) Notice: Subject to any disclaimer, the term of this patent is extended or adjusted under 35 U.S.C. 154(b) by 0 days.

(21) Appl. No.: 14/972,912

(22) Filed: Dec. 17, 2015

(51) Int. Cl.
   *H01R 27/00* (2006.01)
   *A61B 18/12* (2006.01)
   *A61B 18/00* (2006.01)

(52) U.S. Cl.
   CPC ............ *A61B 18/12* (2013.01); *H01R 27/00* (2013.01); *A61B 2018/00077* (2013.01); *A61B 2018/00083* (2013.01)

(58) Field of Classification Search
   CPC ........ H01R 27/00; H01R 27/02; H01R 13/35; A61B 2018/00083; A61B 2018/00077
   USPC .................................. 439/217–223
   See application file for complete search history.

(56) References Cited

U.S. PATENT DOCUMENTS

| | | |
|---|---|---|
| 4,746,298 A | 5/1988 | Hollander |
| 5,573,424 A | 11/1996 | Poppe |
| 5,633,578 A | 5/1997 | Eggers et al. |
| 5,679,022 A | 10/1997 | Cappa et al. |
| 7,131,860 B2 | 11/2006 | Sartor et al. |
| 7,204,727 B2 * | 4/2007 | Germani ............... H01R 4/4827 439/106 |
| 8,021,176 B2 * | 9/2011 | Sekino .................... H01R 27/02 439/222 |
| 8,449,318 B2 | 5/2013 | Beller et al. |
| 8,613,627 B2 | 12/2013 | Selig et al. |
| 8,896,150 B1 * | 11/2014 | Shammoh .............. H01R 13/70 307/31 |
| 2014/0276798 A1 | 9/2014 | Batchelor et al. |

FOREIGN PATENT DOCUMENTS

| | | |
|---|---|---|
| GB | 526733 | 9/1940 |
| WO | 2007/010292 | 1/2007 |

OTHER PUBLICATIONS

Universal Bipolar Cable; www.prima-medical.com/universalbipolar.html; retrieved on Nov. 18, 2015.
Spare Bipolar Cable D Type Universal Forcep Connector; http://www.veterinary-instrumentation.co.uk/product.php-?productid=7089&cat=359&page=1; retrieved on Nov. 18, 2015.

* cited by examiner

*Primary Examiner* — Khiem Nguyen
(74) *Attorney, Agent, or Firm* — Postemak Blankstein & Lund LLP

(57) ABSTRACT

An electrosurgical cable connector that can accept three different styles of electrosurgical forceps connection—a two-pin connection, a two-bladed connection, and a block-bladed connection—is provided for connecting an electrosurgical forceps to an electrosurgical generator.

18 Claims, 9 Drawing Sheets

# ELECTROSURGICAL CABLE CONNECTOR FOR MULTIPLE FORCEPS CONNECTIONS

CROSS REFERENCE TO RELATED APPLICATIONS

N/A

STATEMENT REGARDING FEDERALLY SPONSORED RESEARCH OR DEVELOPMENT

N/A

BACKGROUND

Bipolar electrosurgical forceps have a pair of resilient blades or tines that are used for grasping and coagulating tissue during surgical procedures. The tines are elongated and extend from a first or proximal end to a second or distal end at the tip. In bipolar forceps, each tine of the pair comprises an electrode. Current flows from one tine through the tissue to the other tine. The proximal ends of the tines are electrically connected in any suitable manner, such as by crimping, welding, or soldering, to a pair of terminal pins or blades. The proximal ends of the tines along with the terminal pins or blades are encapsulated using an epoxy-based material or otherwise mounted within an insulating cap. (See FIG. 15.) The forceps are electrically connected to an electrical generator by an electrical cable extending from the generator to the terminal pins or blades at the proximal end of the forceps. The electrical cable has a connector to receive the pins or blades of the forceps.

Three styles of connection at the proximal end of electrical forceps are commonly in use—a two-pin connection, a two-bladed connection, and a block-bladed connection. The two-pin connection, sometimes referred to as a standard US pin connection, includes two electrically conducting pins having a round cross section. The two-bladed connection, sometimes referred to as an "Aesculap style" bladed connection, includes two flat electrically conducting blades. The blades can have a slight recess and lip at the ends. The block-bladed connection, sometimes referred to as a standard European bladed connection, includes two flat electrically conducting blades attached to opposite faces of an insulation block. Each of these types of connections requires a different connector configuration at the end of the electrical cable.

SUMMARY OF THE INVENTION

An electrosurgical cable connector is provided for connecting an electrosurgical forceps to a generator. The cable connector can accept three different styles of forceps connection—a two-pin connection, a two-bladed connection, and a block-bladed connection.

Other aspects of the method and system include the following:
1. A cable connector for connection to an electrosurgical forceps, comprising:
   an electrically insulating housing, a recess within the housing; and
   a pair of electrically conductive receptacles disposed within the recess in the housing, each receptacle comprising:
      a distal end and a proximal end,
      adjacent the distal end, a pair of electrically conducting walls spaced apart to provide a slot therebetween,
      an electrically conductive protrusion formed in a first wall of the pair of walls, the protrusion extending inwardly into the slot and having one or more surfaces thereon disposed for electrical contact with a pin and a blade,
      one of the pair of walls extending proximally beyond an end of the slot to the proximal end of the receptacle, and
      a connection for an electrical wire disposed at the proximal end of the extending wall;
   the receptacles spaced within the recess in the housing with inner walls of the pairs of walls spaced apart and in facing opposition to provide a central aperture therebetween, and the slots providing side apertures on opposite sides of the central aperture.
2. The cable connector of item 1, wherein each receptacle further comprises a biasing member formed in a second wall of the pair of walls opposite the protrusion, the biasing member protruding inwardly into the slot to bias the pin or the blade into contact with the protrusion.
3. The cable connector of item 2, wherein the biasing member comprises a spring.
4. The cable connector of any of items 2-3, wherein the biasing member comprises a resilient, inwardly curved portion of the second wall.
5. The cable connector of any of items 1-4, wherein the electrically conductive protrusion comprises a pair of tabs formed in the first wall.
6. The cable connector of item 5, wherein each receptacle is sized and configured such that a round pin of an electrosurgical forceps can fit within the slot and between the tabs, with the round pin in electrical contact with surfaces of the tabs and a facing surface of a second wall of the pair of walls.
7. The cable connector of any of items 5-6, wherein each receptacle is sized and configured such that a flat blade of an electrosurgical forceps can fit within the slot and between the tabs, with the flat blade in electrical contact with ends of the tabs and a facing surface of a second wall of the pair of walls.
8. The cable connector of any of items 1-7, wherein in each receptacle, the first wall comprises the inner wall.
9. The cable connector of any of items 1-8, wherein each receptacle is insert molded within the housing.
10. The cable connector of any of items 1-9, wherein the connection for the electrical wire comprises a U-shaped extension at the proximal end of each receptacle, for crimping about the electrical wire.
11. The cable connector of any of items 1-10, wherein each receptacle is formed of a single piece of metal.
12. The cable connector of any of items 1-11, wherein each receptacle is formed of stainless steel coated with tin.
13. The cable connector of any of items 1-12, wherein the connector is configured to receive a pair of pins of a two-pin electrosurgical forceps, with each pin receivable within one of the side apertures.
14. The cable connector of any of items 1-13, wherein the connector is configured to receive a pair of blades of a two-bladed electrosurgical forceps, with each blade receivable within one of the side apertures.
15. The cable connector of any of items 1-14, wherein the connector is configured to receive a block-bladed connector of an electrosurgical forceps within the central aperture with contact surfaces of the block-bladed connector in electrical contact with the inner walls of the receptacles.
16. The cable connector of any of items 1-15, wherein the electrically insulating housing is formed of a thermoplastic material.

17. The cable connector of any of items 1-16, wherein each receptacle is electrically connected to an electrical wire of an electrical cable.

18. An electrical cable for connecting between an electrosurgical forceps and a generator for the electrosurgical forceps, comprising:

an electrical cable extending from a proximal end to a distal end;

the cable connector of any of items 1-17 electrically connected to the electrical cable at the distal end of the cable; and a connector for connecting to the generator at the proximal end of the cable.

DESCRIPTION OF THE DRAWINGS

The invention will be more fully understood from the following detailed description taken in conjunction with the accompanying drawings in which.

DETAILED DESCRIPTION OF THE INVENTION

Figure 1:
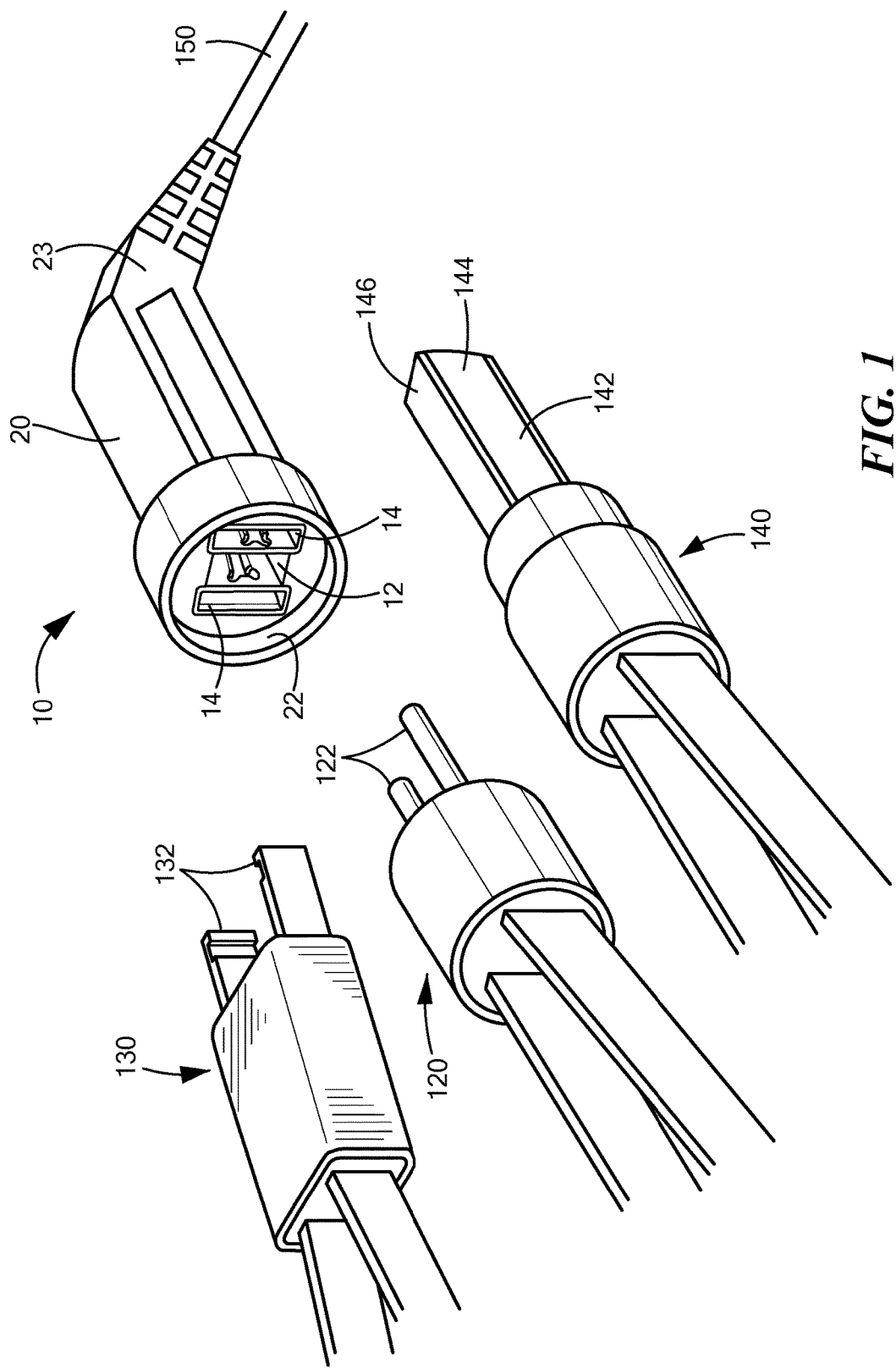
FIG. 1 is an isometric view of an embodiment of an electrosurgical cable connector of the present invention shown with three styles of forceps connection.
Figure 2:
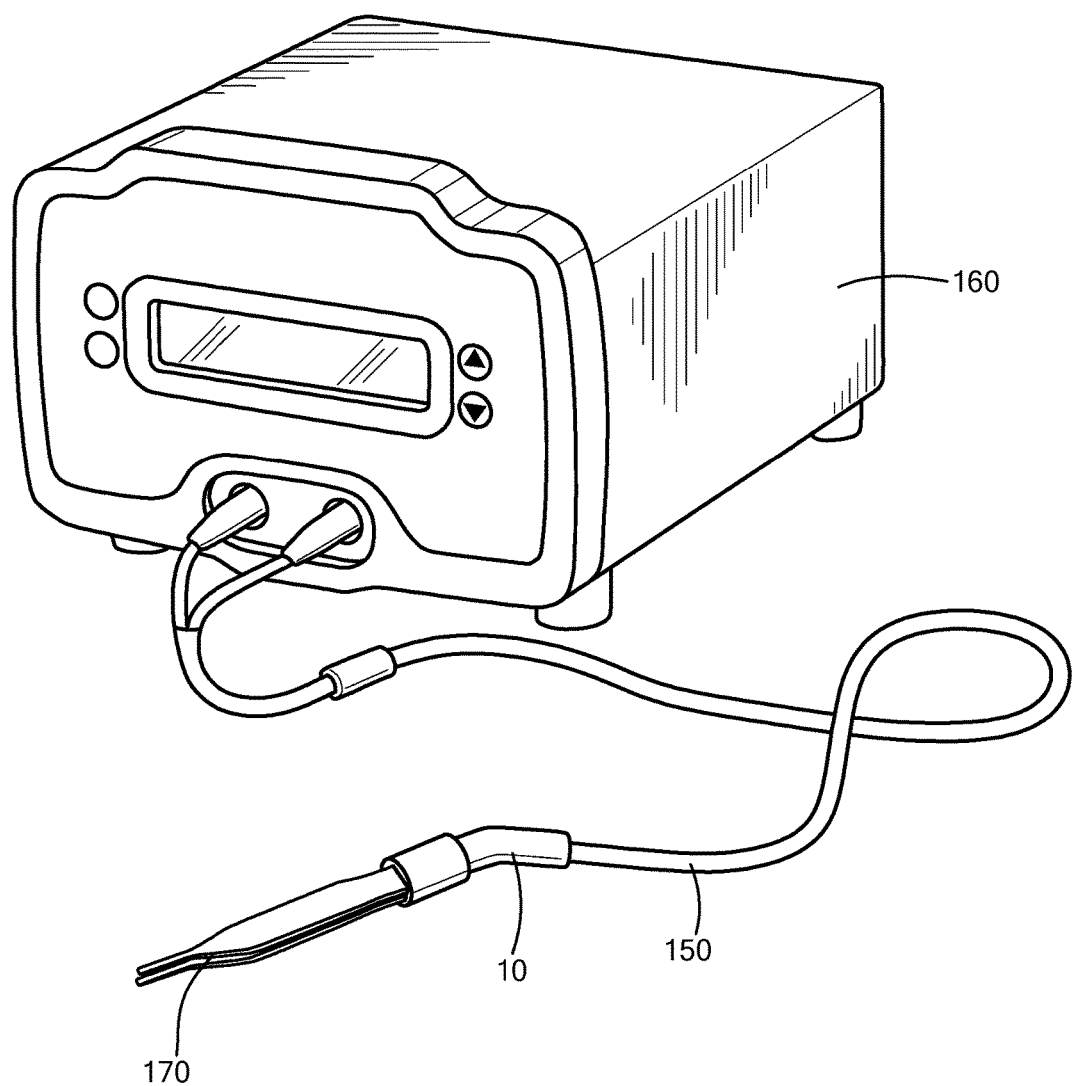
FIG. 2 is an illustration of an electrosurgical forceps electrically connected to an electrosurgical generator by a cable with a cable connector of the present invention.
Figure 3:
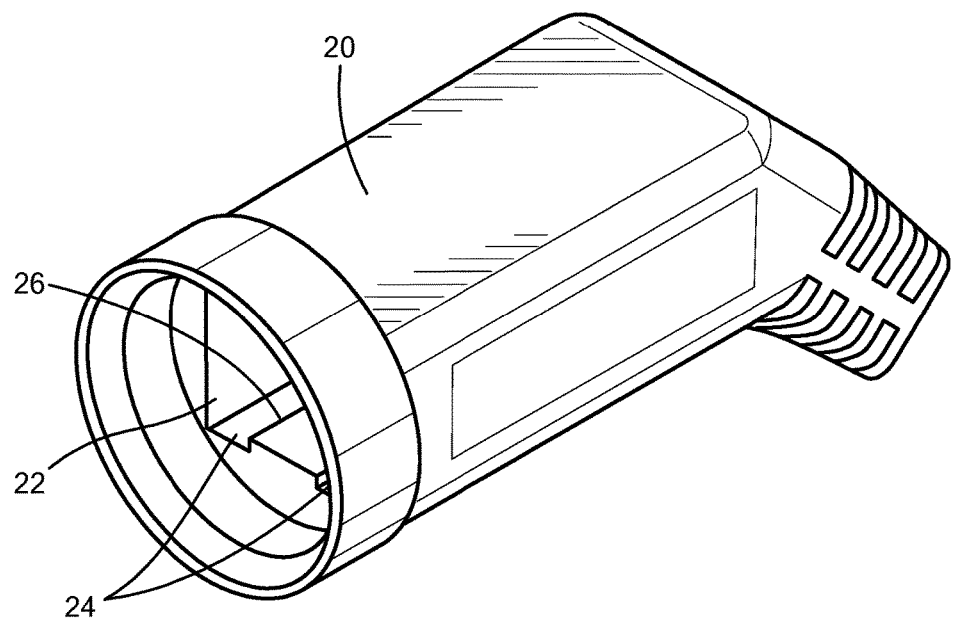
FIG. 3 is an isometric view of a housing of the cable connector of FIG. 1.
Figure 4:
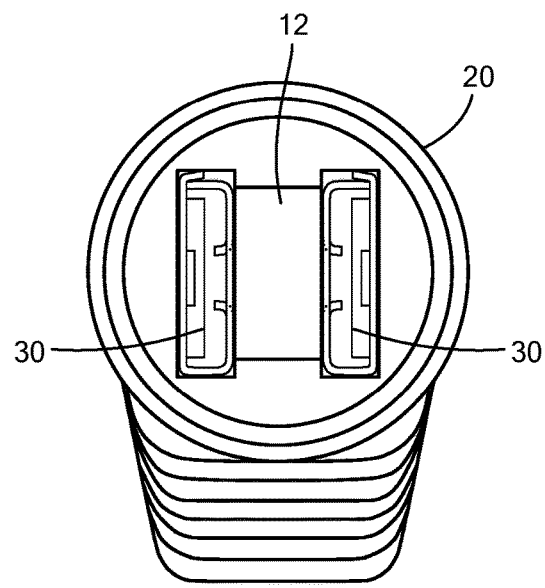
FIG. 4 is a front view of the cable connector of FIG. 1.

An embodiment of a cable connector 10 for electrosurgical forceps is illustrated in FIG. 1 in conjunction with three styles of electrosurgical forceps connection—a two-pin connection 120, a two-bladed connection 130, and a block-bladed connection 140. The cable connector includes a central aperture 12 and two side apertures 14. The block 142 (with electrically conducting blades 144 attached on opposed surfaces of an insulating block 146) of the block-bladed connection 140 can be inserted into the central aperture 12. Each pin 122 of the two-pin connection 120 and each blade 132 of the two-bladed connection 130 can be inserted into one of the two side apertures 14. The cable connector is electrically connected to and forms a distal end of an electrical cable 150 that extends from an electrosurgical generator 160 to an electrosurgical forceps 170. See FIG. 2. As used herein, the distal direction is toward the electrosurgical forceps, and the proximal direction is toward the electrosurgical generator.

Referring more particularly to FIGS. 3-11, the cable connector includes an electrically insulating housing 20 having a recess 22 formed therein. A pair of receptacles 30, each formed of an electrically conducting material, is disposed within the recess 22 in opposed side sections 24 thereof to form the two side apertures 14. The central aperture 12 is formed by a space between the two receptacles 30. The receptacles 30 can be retained in the side sections 24 of the recess 22 in the housing 20 by an edge or lip 26 of the side section adjacent the central aperture.

Figure 5:
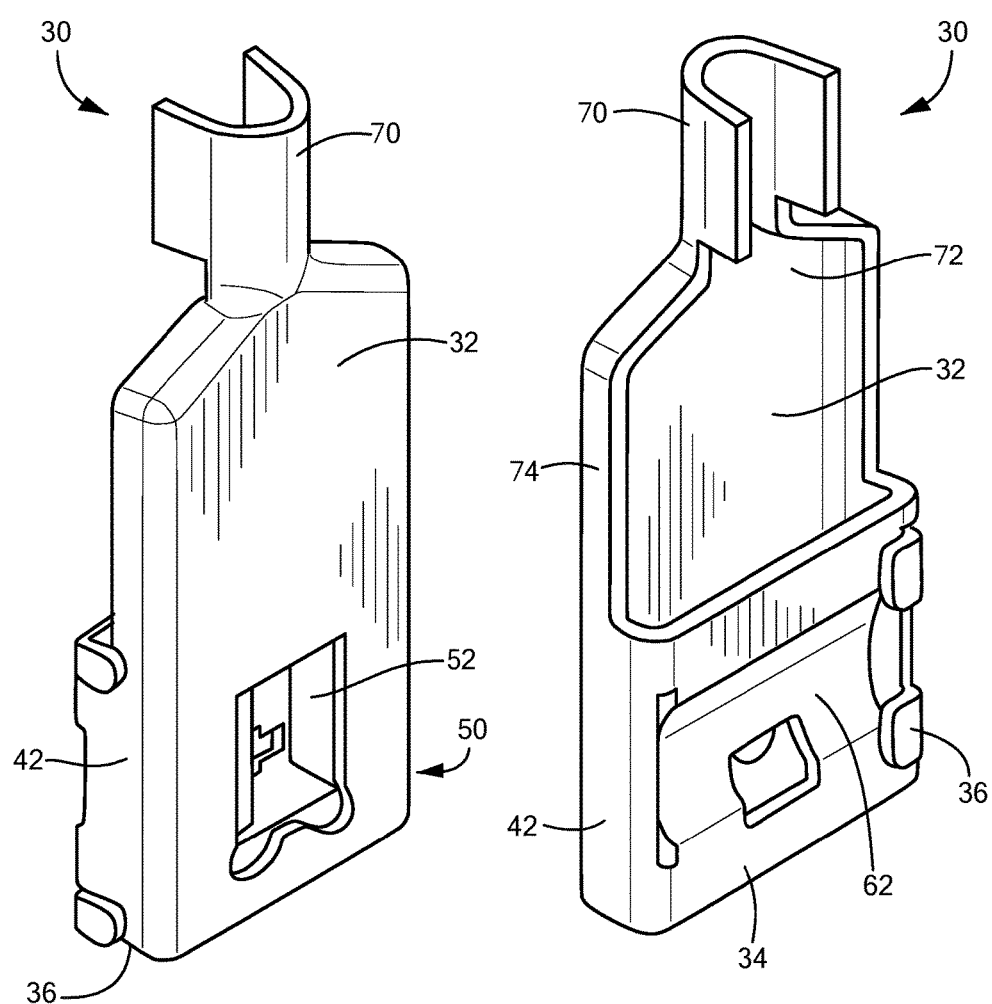
FIG. 5 is an isometric view of a pair of electrically conductive receptacles of the cable connector of FIG. 1.
Figure 6:
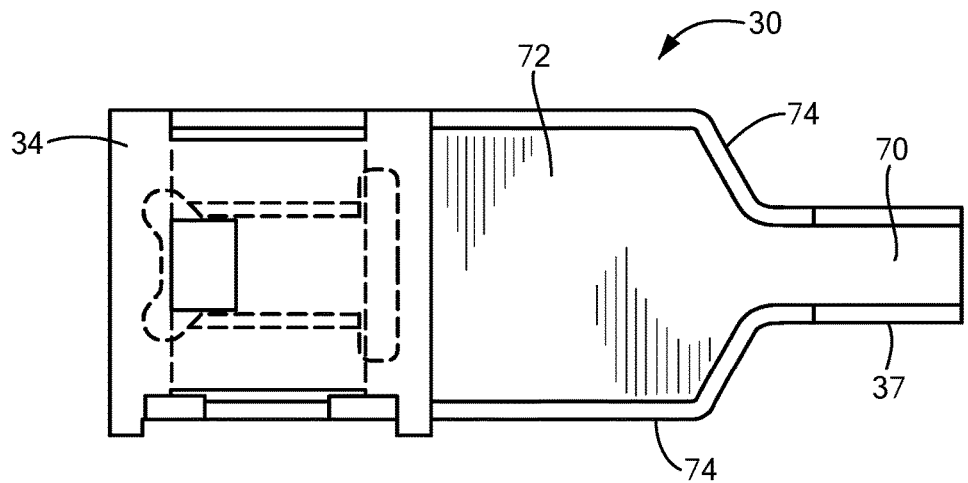
FIG. 6 is top plan view of one of the receptacles of FIG. 5.
Figure 7:
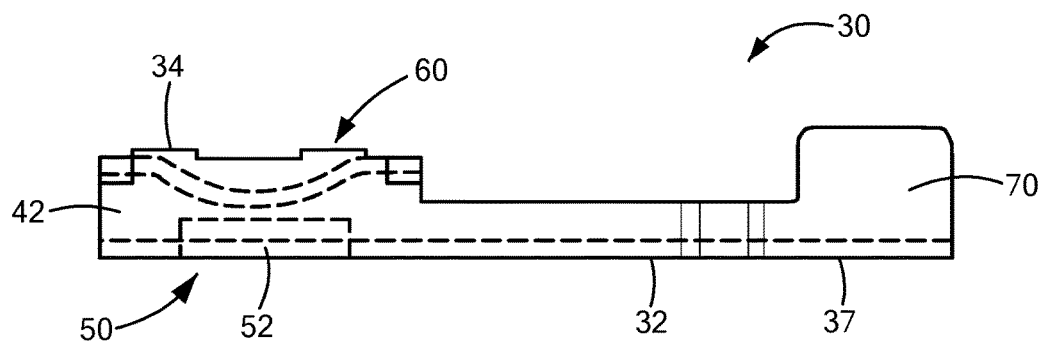
FIG. 7 is a side view of the receptacle of FIG. 6.

In one embodiment, each receptacle 30 includes a pair of electrically conducting walls 32, 34 located adjacent a distal end 36 of the receptacle 30 and spaced apart to provide a slot 38 therebetween. See FIG. 9. The walls can be connected by edge members 42 and can be formed by a single sheet of metal (see FIG. 12) bent to provide a slot configuration between the walls. The slot 38 forms the side aperture 14 and is configured to receive both a pin 122 of a two-pin connection 120 and a blade 132 of a two-bladed connection 130, as described below. The receptacles 30 can be oriented symmetrically within the housing 20, as indicated by FIG. 5. When the receptacle is located in the recess of the housing, the wall 32 forms an inner wall (adjacent the central aperture 12) and the wall 34 forms an outer wall of the receptacle.

An electrically conductive protrusion 50 is formed in or on the inner, first wall 32 of the pair of walls. The protrusion extends inwardly into the slot 38 and has one or more surfaces thereon disposed for electrical contact with the pin and the blade. A biasing member 60 is formed on the outer, second wall 34 of the pair of walls opposite the protrusion. The biasing member protrudes inwardly into the slot 38 to bias the pin or the blade into electrical contact with the protrusion.

In the embodiment illustrated in FIGS. 5-9, the protrusion 50 is formed by a pair of tabs 52 formed in the inner wall 32 to protrude into the slot 38. The biasing member 60 is a spring 62 formed in the outer wall 34 generally opposite to the tabs and biased to protrude into the slot 38.

Figure 10:
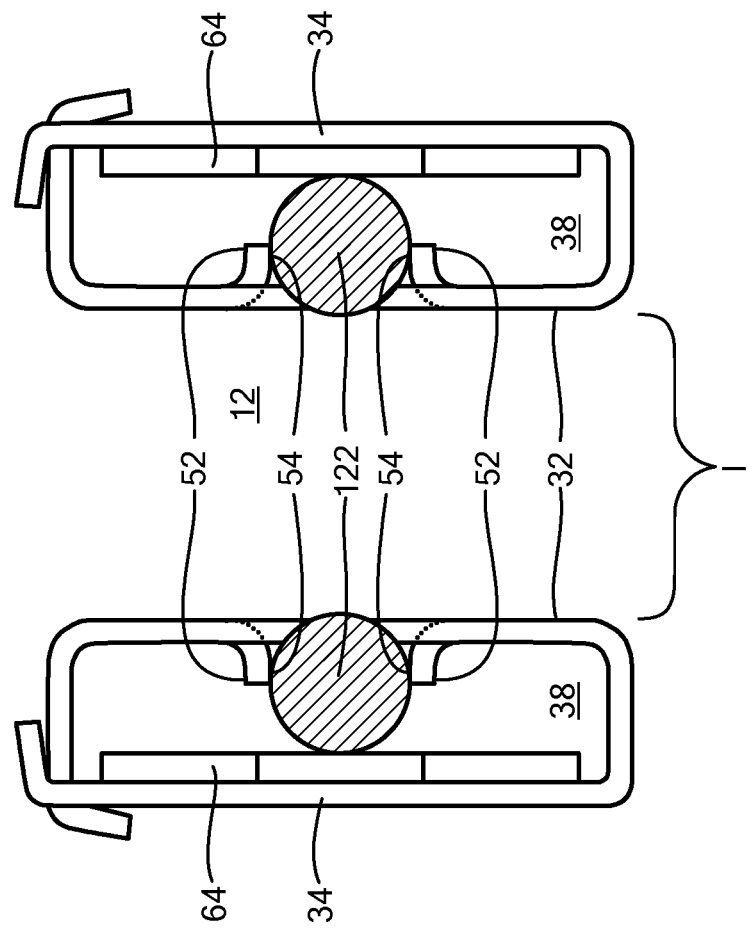
FIG. 10 is an end view of a pair of receptacles with a round pin inserted therein.
Figure 9:
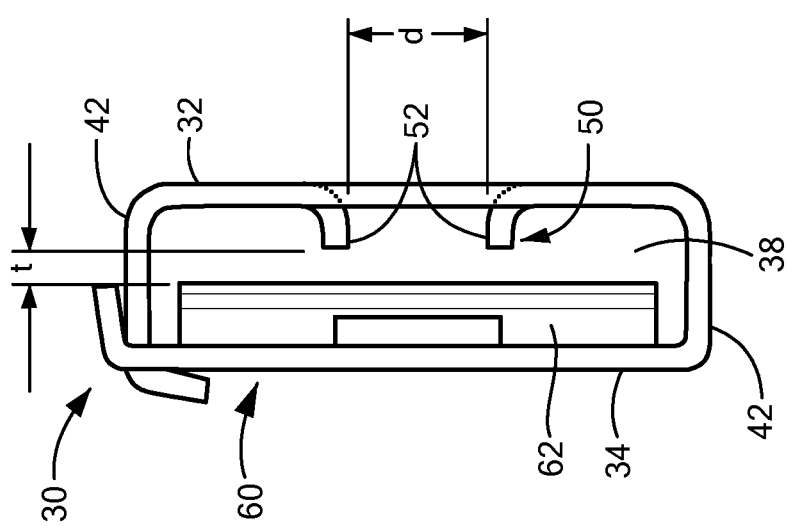
FIG. 9 is an end view of the receptacle of FIG. 6.

The tabs 52 are sized and configured to form a seat for receiving the round pin 122 of a two-pin connection, as best seen in FIGS. 9 and 10. The round pin makes electrical contact with surfaces 54 of the tabs 52 and a surface 64 of the spring 62. The surfaces 54 are spaced apart a distance d equal to or slightly smaller than a diameter of the pin 122. The pin 122 pushes against the bias of the spring 64, assisting in making electrical contact between the pin 122 and the receptacle (with both the tabs 52 and the spring 62) and helping to frictionally retain the pin within the receptacle.

The tabs 52 and the spring 62, in a neutral position (in which no pin 122 or blade 132 is inserted), are spaced apart by a distance t. See FIG. 9. The distance t is equal to or slightly smaller than a thickness of the blade 132 of a two-bladed connector. Thus, when such a blade is inserted into the receptacle, one side of the blade makes electrical contact with tips 56 of the tabs 52 and the other side of the blade makes electrical contact with the surface 64 of the spring 62. See FIG. 11. The resilience of the spring biases the spring into contact with the blade, assisting in making electrical contact between the blade and the receptacle (with both the tabs and the spring) and helping to frictionally retain the blade within the receptacle.

The receptacles are also located within the recess in the housing with a spacing 1 between the inner walls (see FIGS.

10 and 11) that is equal to or slightly smaller than the width of the block-bladed connector. When inserted into the central aperture 12, the blades 142 on the block-bladed connection make electrical contact with the surfaces of the inner walls 32 that face in toward the central aperture. The block-bladed connection can be retained therein within the connector by a friction fit. It will be appreciated that the spacing 1 between the walls 32 of each receptacle 30, the thickness of the walls 32, and the configuration of the tabs and spring can be selected to correspond to the spacing between the pins 122, the blades 132, and the blades 142. For example, the center-to-center spacing of the pins of a standard two-pin connector is typically 0.218 inch.

The wall 32 of each receptacle 30 extends proximally beyond the other wall 34 to a proximal end 37 of the receptacle. A connection 70 for an electrical wire is disposed at the proximal end of the extension 72. See FIGS. 5-8 and 12. The connection for the electrical wire can be a U-shaped extension for crimping about a wire. A lip 74 can be formed along the perimeter of the extension to reduce flexing and bending and impart strength to the receptacle.

The cable connector can be manufactured in any suitable manner. In one embodiment, the receptacle 30 can be formed from a single sheet piece of metal. The receptacle can be stamped or cut from the sheet of metal to have an appropriate shape for bending or folding to form the receptacle. See FIG. 12. In one embodiment, suitable conductive metals include stainless steel that has been hot tin dipped to provide a tin coating. In one embodiment, the thickness of the piece of metal is 0.012 inch.

Figure 8:
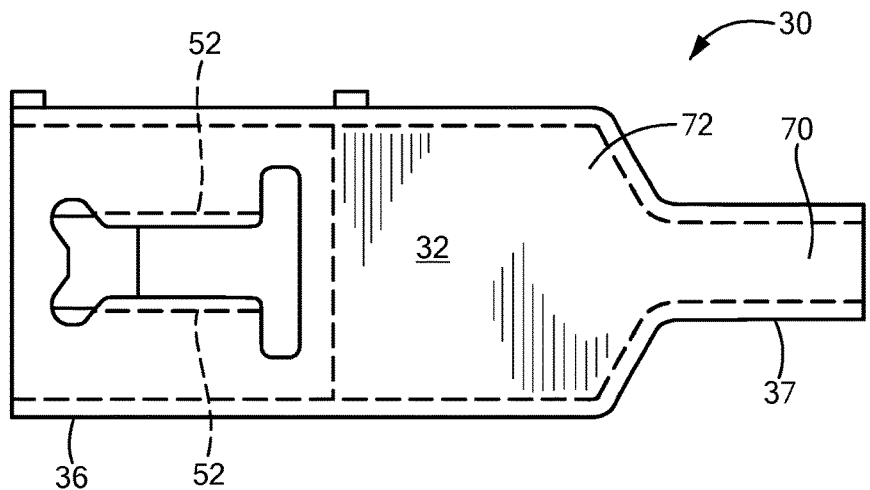
FIG. 8 is a bottom plan view of the receptacle of FIG. 6.
Figure 12:
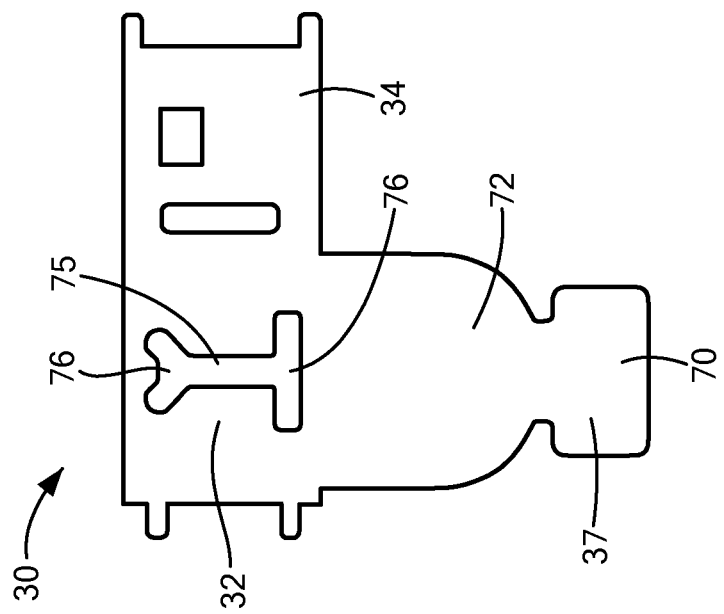
FIG. 12 is a plan view of a receptacle cut from a piece of metal prior to folding.
Figure 11:
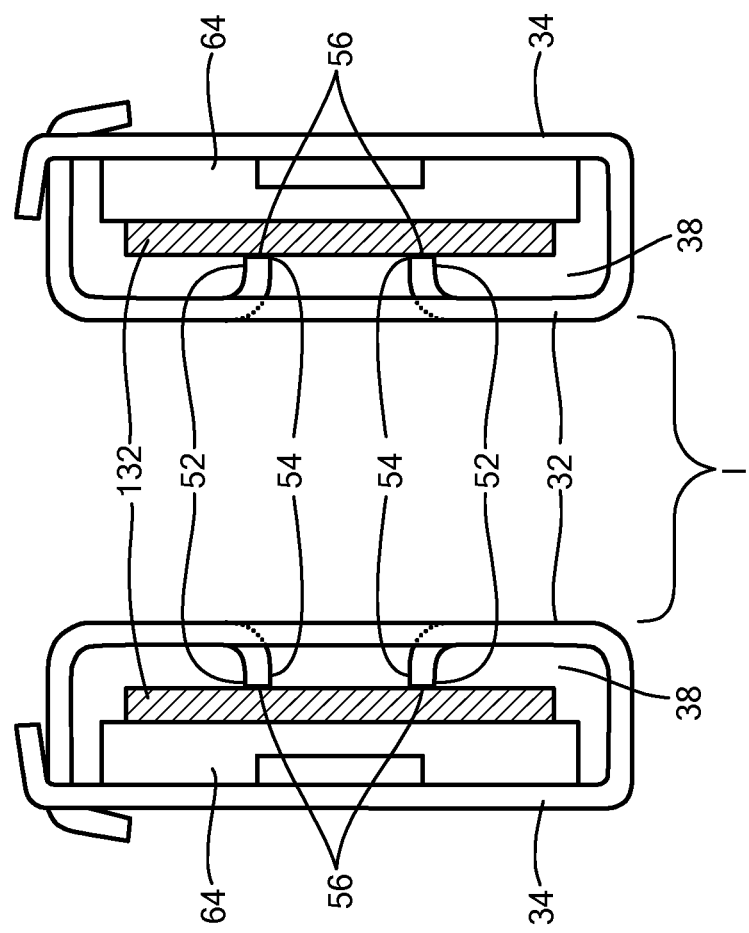
FIG. 11 is an end view of a pair of receptacles with a blade inserted therein.

The tabs 52 can be formed by making a lengthwise slit 75 along a midline of the wall 32 and two transverse widened slits 76 at opposite ends of the lengthwise slit. See FIG. 12. After slitting the inner wall, the tabs can be formed by bending the slit portions inwardly along a fold or bend line extending between the transverse slits. See FIGS. 7-9. The slits can extend past the bend line and/or rounded ends can be formed at the ends of the transverse slits for stress relief, as best illustrated in FIGS. 8 and 12.

The spring 62 can be formed by an inwardly curved portion of the other wall. An opening in the spring adds flexibility. The distal portions of the metal sheet can be bent to form the walls 32, 34 of the slot 38. The connection 70 for an electrical wire at the proximal end can be bent up to a U-shaped configuration.

Figure 13:
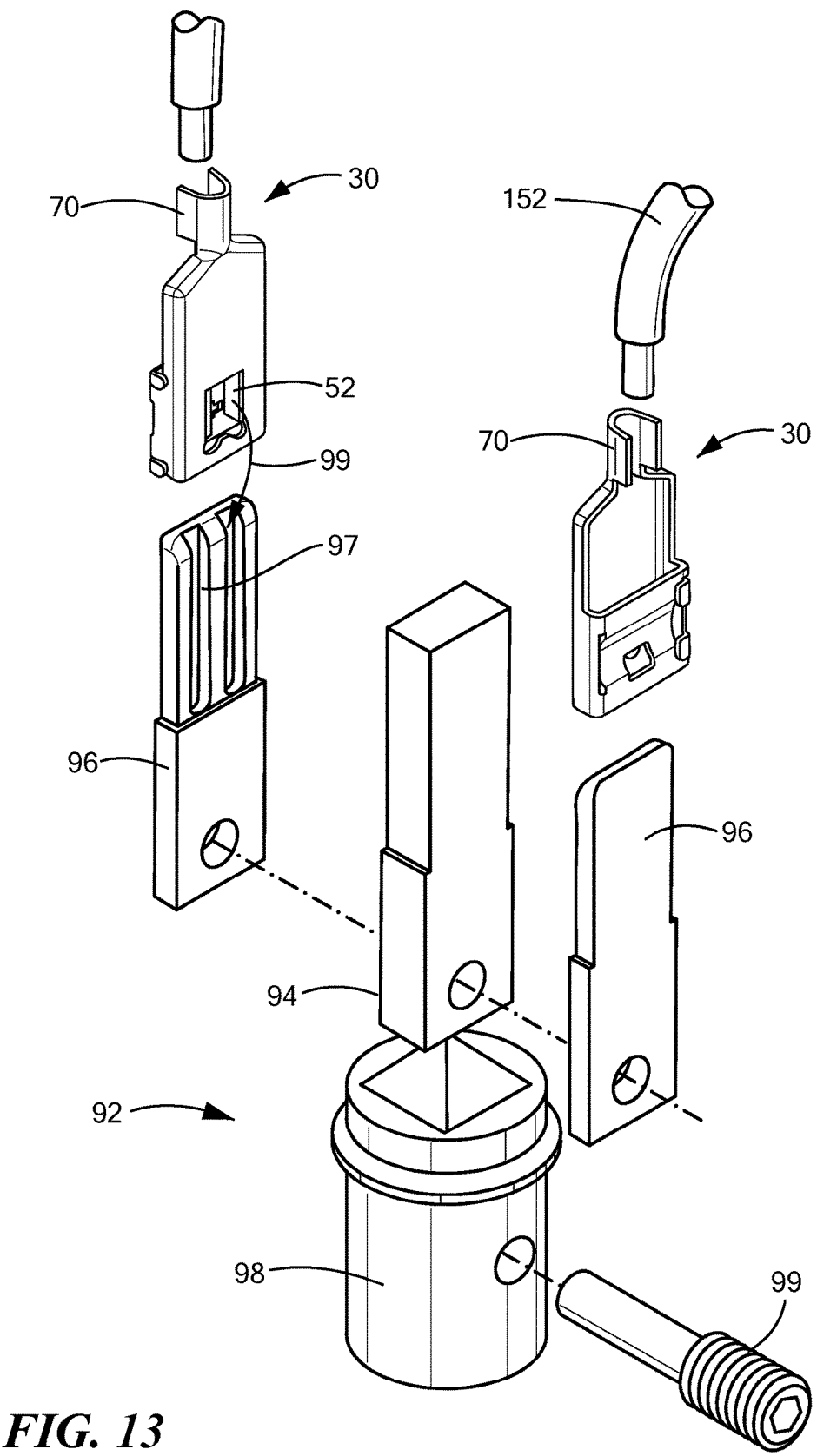
FIG. 13 is an exploded view of a loadbar assembly for manufacturing an embodiment of an electrosurgical cable connector.
Figure 14:
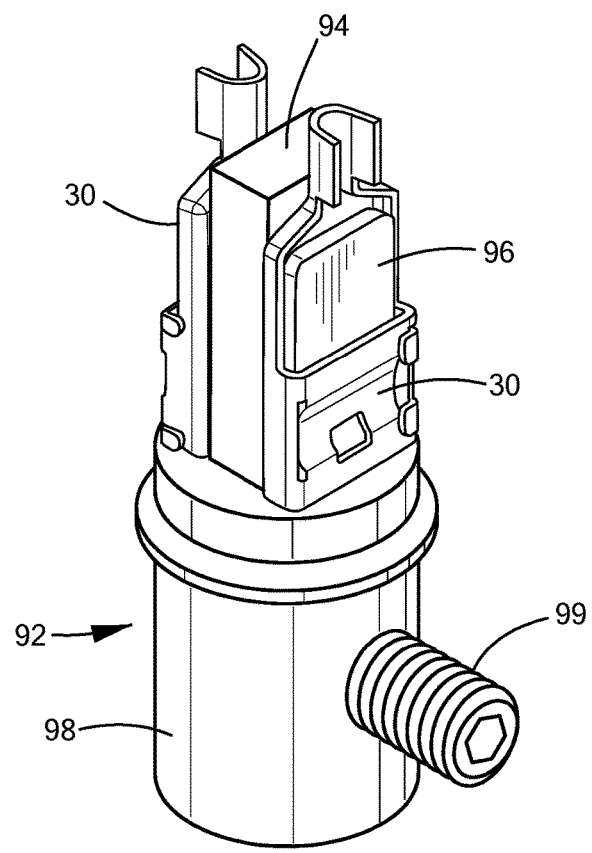
FIG. 14 is an assembled view of the loadbar assembly of FIG. 13.
Figure 15:
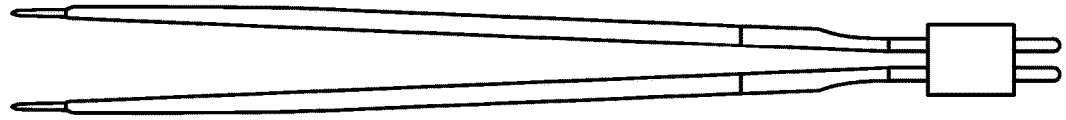
FIG. 15 is a plan view of a prior art electrosurgical forceps with a two-pin connection.

Once the receptacles 30 have been formed, the housing 20 can be insert molded around the receptacles. One embodiment of an insert molding process is described with reference to FIGS. 13 and 14. Two receptacles 30, with uninsulated ends of insulated wires 152 crimped to the connectors, can be mounted in a loadbar assembly 92 for molding. A loadbar middle block 94 fits between two receptacles to maintain the proper spacing between the receptacles. A loadbar receptacle locator 96 fits within each receptacle to prevent molten plastic material for the housing from penetrating the slots 38 to be left empty. The bent-up tabs 52 slide into grooves 97 in the loadbar receptacle locater (indicated schematically by arrow 99) to keep the connector straight. The parts can be mounted in a loadbar insert 98. A modified set screw 99 fits through aligned openings in the loadbar receptacle locators, the loadbar middle block, and the loadbar insert to keep the loadbar receptacle locators and the loadbar middle block from being pulled out of the loadbar insert after molding. The loadbar assembly can be placed in a mold (not shown). A suitable insulating material can be injected into the mold around the receptacles and cured. In some embodiments, the housing 20 can include a shroud 21 at the distal end. See FIGS. 1 and 3. In some embodiments, the housing 20 can have an angled configuration 23 where the cable attaches to the connector, as shown in FIG. 1.

Suitable materials for the housing include, without limitation, thermoplastics such as polyvinyl chloride (suitable for disposable instruments) and thermoplastic vulcanizates such as SANTOPRENE® (suitable for reusable instruments).

As used herein, "consisting essentially of" allows the inclusion of materials or steps that do not materially affect the basic and novel characteristics of the claims. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment. Other configurations of the receptacles can be fabricated as long at the spacing between the pins or blades of each of the types of forceps connection is maintained.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A cable connector for connection to an electrosurgical forceps, comprising:
    an electrically insulating housing, a recess within the housing; and
    a pair of electrically conductive receptacles disposed within the recess in the housing, each receptacle comprising:
        a distal end and a proximal end,
        adjacent the distal end, a pair of electrically conducting walls spaced apart to provide a slot therebetween,
        an electrically conductive protrusion formed in a first wall of the pair of walls, the protrusion extending inwardly into the slot and having one or more surfaces thereon disposed for electrical contact with a pin and a blade,
        one of the pair of walls extending proximally beyond an end of the slot to the proximal end of the receptacle, and
        a connection for an electrical wire disposed at the proximal end of the extending wall;
    the receptacles spaced within the recess in the housing with inner walls of the pairs of walls spaced apart and in facing opposition to provide a central aperture therebetween, and the slots providing side apertures on opposite sides of the central aperture.

2. The cable connector of claim 1, wherein each receptacle further comprises a biasing member formed in a second wall of the pair of walls opposite the protrusion, the biasing member protruding inwardly into the slot to bias the pin or the blade into contact with the protrusion.

3. The cable connector of claim 2, wherein the biasing member comprises a spring.

4. The cable connector of claim 2, wherein the biasing member comprises a resilient, inwardly curved portion of the second wall.

5. The cable connector of claim 1, wherein the electrically conductive protrusion comprises a pair of tabs formed in the first wall.

6. The cable connector of claim 5, wherein each receptacle is sized and configured such that a round pin of an electrosurgical forceps can fit within the slot and between the tabs, with the round pin in electrical contact with surfaces of the tabs and a facing surface of a second wall of the pair of walls.

7. The cable connector of claim 5, wherein each receptacle is sized and configured such that a flat blade of an electrosurgical forceps can fit within the slot and between the tabs, with the flat blade in electrical contact with ends of the tabs and a facing surface of a second wall of the pair of walls.

8. The cable connector of claim 1, wherein in each receptacle, the first wall comprises the inner wall.

9. The cable connector of claim 1, wherein each receptacle is insert molded within the housing.

10. The cable connector of claim 1, wherein the connection for the electrical wire comprises a U-shaped extension at the proximal end of each receptacle, for crimping about the electrical wire.

11. The cable connector of claim 1, wherein each receptacle is formed of a single piece of metal.

12. The cable connector of claim 1, wherein each receptacle is formed of stainless steel coated with tin.

13. The cable connector of claim 1, wherein the connector is configured to receive a pair of pins of a two-pin electrosurgical forceps, with each pin receivable within one of the side apertures.

14. The cable connector of claim 1, wherein the connector is configured to receive a pair of blades of a two-bladed electrosurgical forceps, with each blade receivable within one of the side apertures.

15. The cable connector of claim 1, wherein the connector is configured to receive a block-bladed connector of an electrosurgical forceps within the central aperture with contact surfaces of the block-bladed connector in electrical contact with the inner walls of the receptacles.

16. The cable connector of claim 1, wherein the electrically insulating housing is formed of a thermoplastic material.

17. The cable connector of claim 1, wherein each receptacle is electrically connected to an electrical wire of an electrical cable.

18. An electrical cable for connecting between an electrosurgical forceps and a generator for the electrosurgical forceps, comprising:
   an electrical cable extending from a proximal end to a distal end;
   the cable connector of claim 1 electrically connected to the electrical cable at the distal end of the cable; and
   a connector for connecting to the generator at the proximal end of the cable.

* * * * *